United States Patent [19]

Williams

[11] Plant 4,924

[45] Nov. 9, 1982

[54] ROSE PLANT

[76] Inventor: Ernest D. Williams, 1510 Lebanon Ave., Dallas, Tex. 75208

[21] Appl. No.: 259,894

[22] Filed: May 1, 1981

[51] Int. Cl.[3] ..... A01H 5/00

[52] U.S. Cl. ..... Plt./9

[58] Field of Search ..... Plt./9

*Primary Examiner*—Robert E. Bagwill

[57] ABSTRACT

The subject of this disclosure is a new and distinct variety of miniature rose primarily distinguished by the well shaped pink buds and flowers, produced in abundance and by the bushy, easy to propagate plant.

1 Drawing Figure

The present invention relates to a new and distinct variety of hardy, dwarf, bush type rose plant of the miniature class; the variety being primarily characterized — as to novelty — by buds and flowers of medium pink blended with yellow, which in general color effect are similar to Peaches 'N Cream (miniature — U.S. Plant Pat. No. 4,278).

The variety is further characterized by:

An abundance of bloom, with flowers usually borne singly (sometimes several to the stem).

Some fragrance.

A plant which is vigorous, of rounded much branched shape with small semi-glossy to matte foliage with pointed leaflets; the buds and flowers being similar in form and size to Peaches 'N Cream (miniature — U.S. Plant Pat. No. 4,278).

The plant, which has a normal height of 12 inches or more, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at my nursery located at Dallas, Tex., under conditions of careful control and observation, as a cross between Tom Brown (Floribunda — not patented) as the seed parent and Golden Angel (miniature — U.S. Plant Pat. No. 4,028) as the pollen parent.

Subsequent to origination of the variety I successfully asexually reproduced it at my nursery, located as aforesaid, by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; rounded; seedling; greenhouse; outdoors; cut flowers; garden decoration; potted plant.

Class: Miniature.

*Variety name.*—Bit O'Spring.

Flowers borne: Generally singly (sometimes several together) on slender wirey stems.

Quantity of bloom: Abundant both outside and in greenhouse.

Bud:

*Peduncle.*—Medium length; slender but sturdy; erect; medium green, sometimes tinted bronze (outdoors); hairs — usually several.

*Before calyx breaks.*—Size — small.

*Form.*—Long pointed with several foliaceous appendages and numerous short hairs on surface of bud; with foliaceous parts extending beyond the tip of the bud equal to one-half or less of its length.

*Color.*—Medium green, occasionally tinted with bronze (outdoors).

*As calyx breaks.*—Color — medium to soft pink.

*Opening.*—Opens well in all weather.

Bloom:

*Size when fully open.*—Small, averaging about 1¼".

*Petalage.*—Double — averaging about 45 petals, arranged regularly plus sometimes a few small petaloids.

*Form.*—High centered, becoming more open in the center, with petals rolled loosely outward, and later at maturity full or nearly full with petals rolled loosely outward and downward. Open flowers show few or no stamens.

Petals: Fairly thick; satiny on inside and on outside surface.

*Shape.*—Outside petals, broad lanceolate with rounded (or very short acute) tip; inside — lanceolate with short acute (nearly rounded) tip.

Color: Newly opened flower from a plant grown outdoors (September 1980), Dallas, Tex.

*Outside petal.*—Outside surface — smooth blend of yellow and pink, near Venetian Pink 420/3. Inside surface — near Venetian Pink 420/2 (sometimes deeper shade in cooler weather).

*Intermediate petal.*—Outside surface — similar to outside petal. Inside surface — similar to outside petal.

*Inner petal.*—Outside surface same as intermediate petal; inside surface — same as intermediate petal.

*General color effect.*—Newly opened flowers — clear soft to medium pink. Three days open — color similar to newly opened flowers; becoming progressively lighter pink with tips (upper surface) becoming shaded darker pink. Behavior — opens well in all weather. Spent petals usually drop off. Flower longevity (September 1980) — plant in pot 4–6 days or longer. Cut flowers at living room temperature 3–5 days or longer.

Reproductive organs:

*Stamens.*—Few to average number, arranged regularly about pistils.

*Filaments.*—Varying length.

*Anthers.*—Well formed.

*Pollen.*—Little or none.

*Pistils.*—Average number.

*Styles.*—Fairly even; medium length; bunched.

*Ovaries.*—All enclosed in calyx.

*Hips.*—None.

*Sepals.*—Permanent; spear shaped; recurved.

*Seed.*—None.

Foliage:

*Leaves.*—Compound of five (sometimes three) leaflets; small leather; semi-glossy to matte.

*Leaflets.*—Shape: broad, nearly oval; apex acute; base rounded or rounded acute. Margin serrate. Color: dark green; new growth — normal (medium) green. Rachis: medium strength; upper side may have several tiny short hairs, grooved, underside; several small thorns with some tiny hairs.

*Stipules.*—Short to medium long; narrow to medium width; medium length; narrow points which turn out at more or less than 45 degrees.

Growth:

*Habit.*—Dwarf; bushy; rounded; much branched.

*Growth.*—Free vigorous; internodes short.

*Canes.*—Medium; slender; sturdy.

*Main stems.*—Color: medium green.

*Thorns.*—Average; slender; hooked slightly downward; color: tan. Prickles — none. Hairs — none.

The miniature rose plant and its flowers as herein described may vary in slight detail due to climatic, soil and cultural conditions under which the variety may be grown; the present description being of the variety as grown at Dallas, Tex.

The following is claimed:

1. A new and distinct variety of miniature rose plant of hardy, dwarf, bushy, much branched habit, substantially as illustrated and described, characterized by buds and flowers which are medium to light pink in color (being a blend of soft pink and yellow), the buds and flowers resembling Peaches 'N Cream (miniature — U.S. Plant Pat. No. 4,278), in color, size and shape; and further characterized by a plant which is vigorous and compact, easy to propagate from cuttings or by budding; with an abundance of small semi-glossy to matte foliage and an abundance of flowers borne singly (sometimes several) on sturdy slender stems.

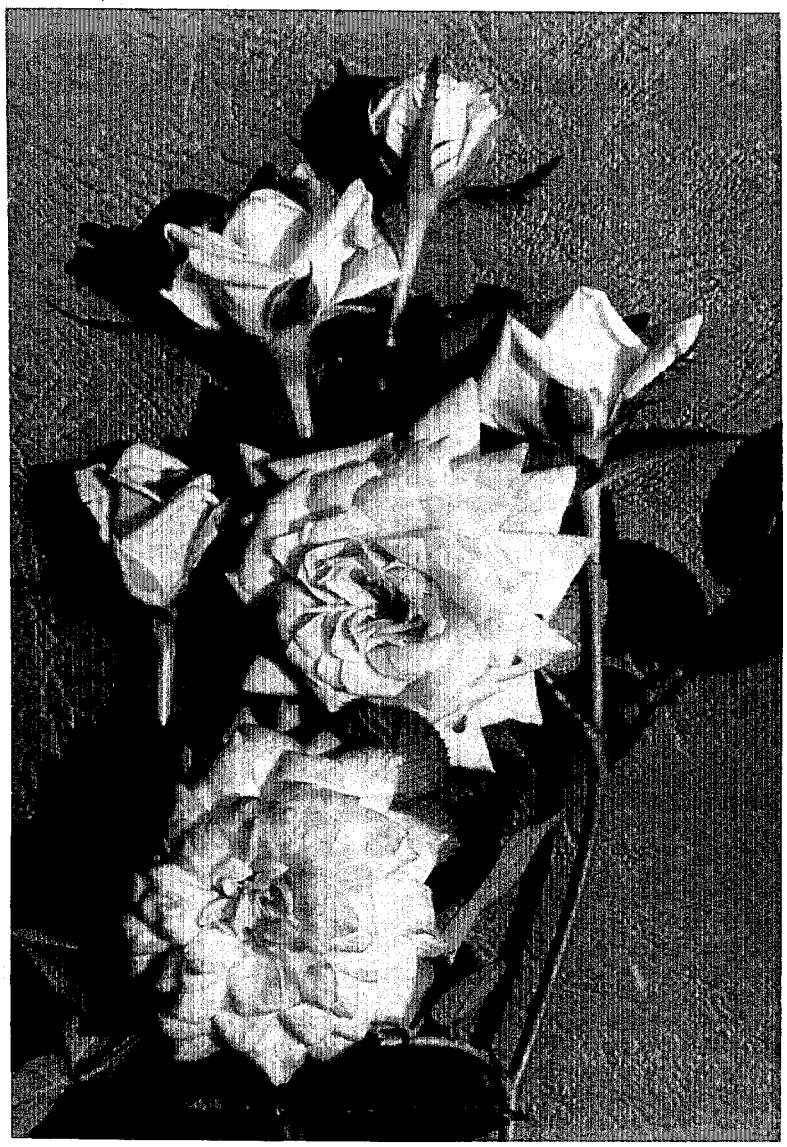

* * * * *